United States Patent
Ackerman

(10) Patent No.: US 7,228,163 B2
(45) Date of Patent: Jun. 5, 2007

(54) METHODS OF MONITORING GLUCOSE LEVELS IN A SUBJECT AND USES THEREOF

(75) Inventor: Neil Ackerman, San Carlos, CA (US)

(73) Assignee: Animas Technologies, LLC, West Chester, PA (US)

( * ) Notice: Subject to any disclaimer, the term of this patent is extended or adjusted under 35 U.S.C. 154(b) by 177 days.

(21) Appl. No.: 10/982,549

(22) Filed: Nov. 5, 2004

(65) Prior Publication Data

US 2005/0124874 A1    Jun. 9, 2005

Related U.S. Application Data

(63) Continuation of application No. 10/421,440, filed on Apr. 23, 2003, now Pat. No. 6,862,466, which is a continuation of application No. 09/927,576, filed on Aug. 10, 2001, now abandoned.

(60) Provisional application No. 60/228,617, filed on Aug. 28, 2000.

(51) Int. Cl.
*A61B 5/05* (2006.01)
*A61B 5/00* (2006.01)

(52) U.S. Cl. .................... 600/347; 600/365; 600/345
(58) Field of Classification Search ........ 600/345–348, 600/353, 354, 362, 364, 365, 366
See application file for complete search history.

(56) References Cited

U.S. PATENT DOCUMENTS

| | | | |
|---|---|---|---|
| 4,686,624 | A | 8/1987 | Blum et al. |
| 4,703,756 | A | 11/1987 | Gough et al. |
| 4,731,726 | A | 3/1988 | Allen |
| 5,279,543 | A | 1/1994 | Glikfeld et al. |
| 5,362,307 | A | 11/1994 | Guy et al. |
| 5,458,140 | A | 10/1995 | Eppstein et al. |
| 5,462,051 | A | 10/1995 | Oka et al. |
| 5,507,288 | A | 4/1996 | Bocker et al. |
| 5,569,186 | A | 10/1996 | Lord et al. |

(Continued)

FOREIGN PATENT DOCUMENTS

EP    0 290 683    11/1988

(Continued)

OTHER PUBLICATIONS

Newman et al., "Catalytic Materials, Membranes, and Fabrication Technologies Suitable for the Construction of Amperometric Biosensors," *Analytical Chemistry* 67:4594-4599 (1995).

(Continued)

*Primary Examiner*—Charles A. Marmor, II
*Assistant Examiner*—Navin Natnithithadha
(74) *Attorney, Agent, or Firm*—Bernard E. Shay

(57) ABSTRACT

Methods of frequently monitoring glucose amounts and/or concentrations in a subject who is at risk for hypoglycemia, hyperglycemia, and/or glucose level fluctuations that put the subject at risk are provided. Also provided are methods of monitoring the effects of one or more pharmaceutical compositions on the levels of glucose in a subject.

4 Claims, 1 Drawing Sheet

U.S. PATENT DOCUMENTS

| | | | |
|---|---|---|---|
| 5,730,714 | A | 3/1998 | Guy et al. |
| 5,735,273 | A | 4/1998 | Kurnik et al. |
| 5,747,806 | A | 5/1998 | Khalil et al. |
| 5,771,890 | A | 6/1998 | Tamada |
| 5,822,715 | A | 10/1998 | Worthington et al. |
| 5,827,183 | A | 10/1998 | Kurnik et al. |
| 5,914,701 | A | 6/1999 | Gersheneld et al. |
| 5,954,685 | A | 9/1999 | Tierney |
| 5,989,408 | A | 11/1999 | Bacrts et al. |
| 6,023,629 | A | 2/2000 | Tamada |
| 6,024,699 | A | 2/2000 | Surwit et al. |
| 6,139,718 | A | 10/2000 | Kurnik et al. |
| 6,141,573 | A | 10/2000 | Kurnik et al. |
| 6,144,869 | A | 11/2000 | Berner et al. |
| 6,180,416 | B1 | 1/2001 | Kurnik et al. |
| 6,201,979 | B1 | 3/2001 | Kurnik et al. |
| 6,233,471 | B1 | 5/2001 | Berner et al. |
| 6,272,364 | B1 | 8/2001 | Kurnik |
| 6,284,126 | B1 | 9/2001 | Kurnik et al. |
| 6,298,254 | B2 | 10/2001 | Tamada |
| 6,299,578 | B1 | 10/2001 | Kurnik et al. |
| 6,309,351 | B1 | 10/2001 | Kurnik et al. |
| 6,326,160 | B1 | 12/2001 | Dunn et al. |
| 6,356,776 | B1 | 3/2002 | Berner et al. |
| 6,379,301 | B1 | 4/2002 | Worthington et al. |
| 6,633,772 | B2 | 10/2003 | Ford et al. |
| 2003/0208113 | A1 * | 11/2003 | Mault et al. ........... 600/316 |

FOREIGN PATENT DOCUMENTS

| | | |
|---|---|---|
| EP | 0 462 466 | 4/1997 |
| WO | WO 96/00109 | 1/1996 |
| WO | WO 97/02050 | 1/1997 |
| WO | WO 97/02811 | 1/1997 |
| WO | WO 97/28737 | 8/1997 |
| WO | WO 99/58050 | 11/1999 |
| WO | WO 99/58190 | 11/1999 |
| WO | WO 00/47109 | 8/2000 |
| WO | WO 00/78208 | 12/2000 |

OTHER PUBLICATIONS

Bolinder et al., "Self-Monitoring of Blood Glucose in Type I Diabetic Patients: Comparison with Continuous Microdialysis Measurements of Glucose In Subcutaneous Adipose Tissue During Ordinary Life Conditions," *Diabetes Care* 20(1):64-70 (1997).

Ohkubo et al., "Intensive Insulin Therapy Prevents the Progression of Diabetic Microvascular Complications in Japanese patients with Non-Insulin-Dependent Diabetes Mellitus: a Randomized Prospective 6-year Study," *Diabetes Research & Clinical Practice* 28:103-117 (1995).

UK Prospective Diabetes Study (UKPDS) Group., "Effect of Intensive Blood-Glucose Control With Metformin on Complications in Overweight Patients with Type 2 Diabetes (UKPDS 34)," *Lancet* 352:837-853 (1998).

Tamada et al., "Noninvasive Glucose Monitoring," *JAMA* 282:1839-1844 (1999).

Updike et al., "The Enzyme Electrode," *Nature* 214:986-988 (1967).

Ludwig D S et al.,"Dietary Glycemic Index and Obesity.",*Journal of Nutrition*, 130,(2S):280S-283S (2000).

Ludwig D S et al., "High Glycemic Index Foods, Overeating, and Obesity.", *Pediatrics*, 103,(3): E26 (1999).

Astrup Ame et al., "Glucostatic Control of Intake and Obesity", *Proceedings of the Nutrition Society*, 55 (1B): 485-495 (1996).

Kopelman, "Obesity as a Medical Problem" *Nature* 404:635-643 (2000).

* cited by examiner

METHODS OF MONITORING GLUCOSE LEVELS IN A SUBJECT AND USES THEREOF

CROSS-REFERENCE TO RELATED APPLICATIONS

This application is a continuation of U.S. patent application Ser. No. 10/421,440, filed 23 Apr. 2003 now U.S. Pat. No. 6,862,466, which is a continuation of U.S. patent application Ser. No. 09/927,576, filed 10 Aug. 2001, now abandoned which claims the benefit of U.S. Provisional Application Ser. No. 60/228,617, filed 28 Aug. 2000, all which applications are incorporated herein by referenced in their entireties.

TECHNICAL FIELD

The present invention is in the field of medical devices and methods of use thereof. More particularly it relates to methods of using glucose monitoring devices to monitoring glucose amounts and/or concentrations in a subject who is at risk for hypoglycemia, hyperglycemia, or fluctuations toward hypoglycemia and/or hyperglycemia. The methods also include methods of monitoring the effects of one or more pharmaceutical compositions on the levels of glucose in a subject.

BACKGROUND OF THE INVENTION

The level, presence, and/or absence of glucose in a subject can have a number of consequences. For example, fluctuations of blood glucose levels can result in one of two physiological states, hypoglycemia and hyperglycemia. Hypoglycemia is defined as plasma glucose levels below normal. Hypoglycemia can be symptomatic or asymptomatic. For example, subjects suffering from postprandial hypoglycemia generally have symptoms of adrenergic stimulation including diaphoresis, anxiety, irritability, palpitations, tremor, and hunger. Such symptoms typically occur from about 2 to 4 hours postprandially and tend to occur suddenly with symptoms generally subsiding in about 15 to 20 minutes. Hypoglycemia can be caused by release of adrenergic and cholinergic hormones. Postprandial hypoglycemia is often idiopathic, however, it can be caused by early diabetes, alcohol intake, renal failure, and drug treatments. In addition, a category of hypoglycemia exists which is designated as fasting hypoglycemia. Clinically, this form of hypoglycemia may have symptoms of neuroglycopenia including headache, fatigue, and mental dullness. In more severe cases, hypoglycemia can progress to confusion, blurring of vision, seizure, and ultimately loss of consciousness or seizure. Fasting hypoglycemia can occur with a fast of greater than 4 hours, and further can be caused by insulinoma (resulting from self-administered insulin or intake of other hypoglycemic agents, alcohol abuse, liver disease (e.g., decreased gluconeogenesis), pituitary insufficiency, or adrenal insufficiency).

Hyperglycemia, on the other hand, refers to excessive levels of blood glucose in a subject. There are many forms of hyperglycemia, the primary form being diabetes mellitus (DM) which is defined as hyperglycemia secondary to decreased insulin production or an increase in peripheral tissue resistance to the action of insulin. There are several classifications of DM including, type 1 DM, type 2 DM, gestational DM, and secondary DM (which can, for example, be the result of a variety of drug therapies, disease states (e.g., pancreatitis, Cushing's syndrome), trauma, surgery, and others causes). Further, in the case of severe insulin deficiency, a starvation-like state develops resulting in acidosis (typically referred to as diabetic ketoacidosis). Symptoms of ketoacidosis can include rapid respiration, acetone breath, vomiting, dehydration, nausea, abdominal pain and changes in mental stability.

Thus, there is a need for frequent monitoring of glucose levels in many subjects who are at risk for hypogylcemia and hyperglycemia.

SUMMARY OF THE INVENTION

The present invention describes methods of monitoring glucose levels and/or concentration in a subject having a disease state or condition which puts the subject at risk for hypoglycemia, hyperglycemia, or fluctuations toward hypoglycemia and/or hyperglycemia (for example, quickly dropping or increasing glucose levels). A wide variety of disease states or conditions benefit from frequent glucose monitoring, such monitoring provides a tool for the subject, and/or healthcare professional, to develop a response or plan to assist with management of the disease state or condition. Methods of monitoring a subject for the effects of at least one non-insulin containing pharmaceutical composition on glucose amount or levels in subjects are also described. The subject being monitored may also be receiving insulin-containing compositions.

In one aspect the invention includes, a method for monitoring an amount or concentration of glucose in a subject having a disease state or condition, the method comprising: extracting glucose from the subject having the disease state or condition into a reservoir to obtain an amount or concentration of glucose in the reservoir, wherein the extracting is carried out using an iontophoresis system comprising first and second iontophoretic electrodes; contacting extracted glucose extracted with glucose oxidase that reacts with glucose to produce hydrogen peroxide; detecting the hydrogen peroxide with a sensor element that reacts electrochemically with the hydrogen peroxide to produce a detectable signal; measuring the signal produced; correlating the measured signal with an amount or concentration of glucose in the subject; and performing the extracting, detecting, and measuring frequently, and performing the correlating at least periodically to monitor glucose amount or concentration in the subject in order to assist in management of the disease state or condition. The methods are helpful to the subject, and/or healthcare professional, to provide responses or plans to assist in the management of a wide variety of disease states and conditions, including, but not limited to, a weight management regime; cancer remission; infection with human immunodeficiency virus (HIV); infection with *Candida*; long distance driving; organ transplantation; growth hormone therapy; renal failure; infection with malaria; alcoholism; intense exercise; cardiovascular disease; cystic fibrosis; or stroke or ischemia. Further, such methods are helpful in assisting in the management of diabetic disease states (e.g., gestational diabetes; fetal or premature-birth neonate (i.e., a neonate born before term) glucose management).

In one aspect, the present invention comprises a method for evaluating compliance with a weight management program in a subject. In this method a reference range of glucose amounts or concentrations is determined that correspond to achieving a weight management goal in the subject. Such range of glucose amounts or concentrations typically comprises a high threshold glucose value and a low threshold glucose value. Further, rates of change (or trends) of glucose amounts or concentrations in the subject may be determined. In one embodiment of the present invention, monitoring of glucose amount or concentration in the subject is accomplished by a glucose monitoring method comprising the following. First a sample is extracted from the subject, where the sample comprises glucose. The extraction is carried out, for example, transdermally. In one embodiment, the transdermal sampling system is in operative contact with a skin or mucosal surface of the subject, and may be maintained in contact to obtain a series of samples, for example, the extracting is carried out using an iontophoretic system comprising first and second iontophoretic electrodes. The extracted sample is contacted with a sensor element, for example, in the presence of glucose oxidase that reacts with glucose to produce hydrogen peroxide. The hydrogen peroxide is detected by the sensor element, for example, by an electrochemical reaction between the sensor element and the hydrogen peroxide, thus a detectable signal is produced. The detectable signal is specifically related to glucose amount or concentration in the subject. The detectable signal is measured and correlated with an amount or concentration of glucose in the subject. The glucose monitoring method is typically repeated to obtain a series of glucose amounts or concentrations, in the subject, at selected time intervals. Glucose monitoring is usually carried out frequently and periodically. Exemplary devices for use in glucose monitoring are described herein. The glucose monitoring device used in the method of the present invention may have alert means, where an alert is provided to the subject (for example, an auditory alert) when glucose levels exceed the predetermined threshold values, when glucose levels change at a rate faster than a predetermined rate of change, or when a predicted glucose value for a later time point falls outside of the predetermined range. The subject typically maintains a record of caloric intake. Such a record may be inputted into the glucose monitoring device itself, or a related device (such as a personal digital assistant, where, for example, the personal digital assistant is operatively connected, at least periodically, with the record of glucose values obtained by the glucose monitoring device). Alternately, such a record may be manually maintained. In addition to caloric intake, caloric output may be recorded as well. This record is then compared to the series of glucose amounts or concentrations and the predetermined reference ranges to evaluate compliance with the reference range of glucose amounts or concentrations to achieve the weight management goal of the subject.

The weight management goal may be weight gain in the subject, weight reduction in the subject, and weight maintenance in the subject.

A further aspect of the present invention comprises a method for monitoring an effect of at least one non-insulin-containing pharmaceutical composition on glucose levels in a subject receiving the pharmaceutical composition. In the method, glucose monitoring in the subject may be carried out by the method described above. In this method a record is maintained of treatment with the pharmaceutical composition. The series of glucose amounts or concentrations and the record are compared to evaluate the effect of the pharmaceutical composition on glucose levels in the subject receiving the pharmaceutical composition. A reference range of glucose amounts or concentrations is typically determined that corresponds to maintaining a desired range of glucose amounts or concentrations in the subject during a treatment course with the pharmaceutical composition. The reference range comprises, for example, a high threshold glucose value, a low threshold glucose value, a predetermined rate of change (e.g., glucose levels change at a rate faster than a predetermined rate of change), and/or a predicted glucose value for a later time point. The glucose monitoring device may provide an alert corresponding to threshold values, rate changes, a predicted glucose value that falls outside of the predetermined range, etc. Such glucose monitoring is useful when any one or more of a number of pharmaceutical compositions are being used to treat a subject. Exemplary pharmaceutical compositions are described herein and include, but are not limited to, pentamidine, quinine, saquinavir, and/or indomethacin. In addition, the subject may also be receiving insulin, or another pharmaceutical directly targeted to maintenance of glucose levels in the subject.

Another aspect of the present invention relates to a method for improving prognosis and/or reduction of adverse side-effects associated with a disease state or condition in a subject. In this aspect of the present invention, a reference range of glucose amounts or concentrations is determined that corresponds to achieving an improved prognosis or reduction of adverse side-effects associated with the disease state or condition in the subject. The reference range comprises, for example, a high threshold glucose value, a low threshold glucose value, a predetermined rate of change (e.g., glucose levels change at a rate faster than a predetermined rate of change), and/or a predicted glucose value for a later time point. The glucose monitoring device may provide an alert corresponding to threshold values, rate changes, a predicted glucose value that falls outside of the predetermined range, etc. The series of glucose amounts or concentrations and the reference range are compared to evaluate compliance with the reference range of glucose amounts or concentrations to achieve an improved prognosis or reduction of adverse side-effects associated with the disease state or condition in the subject. In this aspect of the present invention, the disease state or condition is not type I or type II diabetes.

Exemplary disease states or conditions are described herein and include, but are not limited to, cancer remission, infection with human immunodeficiency virus (HIV), infection with *Candida* and/or other systemic pathogens, long distance driving, organ transplantation, growth hormone therapy, renal failure, infection with malaria, alcoholism, intense exercise or training, cardiovascular disease, cystic fibrosis, stroke or ischemia, and/or an eating disorder.

These and other embodiments of the present invention will readily occur to those of ordinary skill in the art in view of the disclosure herein.

DETAILED DESCRIPTION OF THE INVENTION

Figure 1:
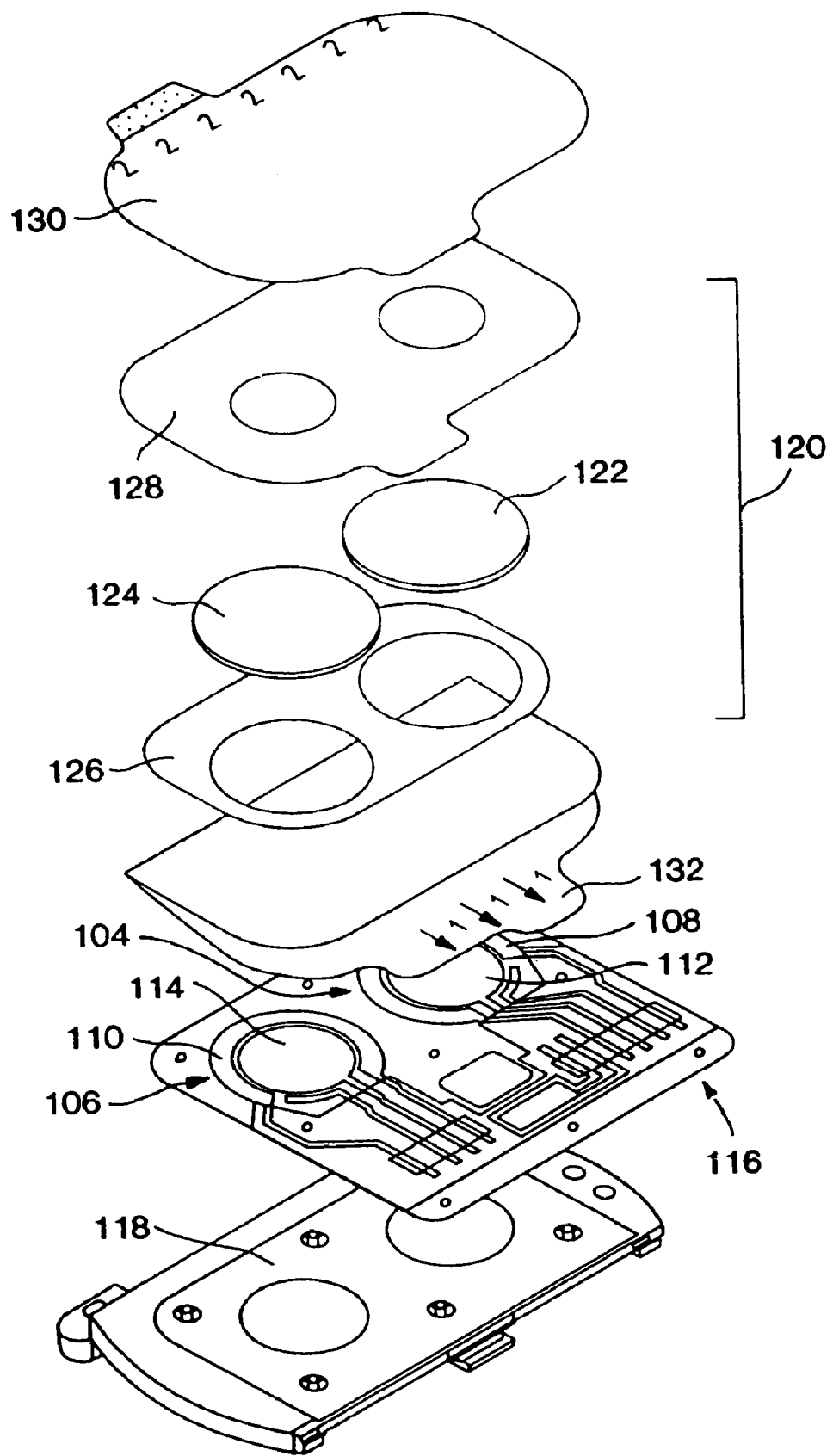
FIG. 1 presents a schematic of an exploded view of exemplary components comprising one embodiment of an AutoSensor for use in an analyte monitoring system.

The practice of the present invention will employ, unless otherwise indicated, conventional methods and techniques of chemistry, biochemistry, electrochemistry and pharmacology, within the skill of the art. Such conventional methods and techniques are explained fully in the literature.

All publications, patents and patent applications cited herein, whether above or below are hereby incorporated by reference in their entirety.

1. Definitions

It is to be understood that the terminology used herein is for the purpose of describing particular embodiments only, and is not intended to be limiting. As used in this specification and the appended claims, the singular forms "a", "an" and "the" include plural referents unless the context clearly dictates otherwise. Thus, for example, reference to "a reservoir" includes a combination of two or more such reservoirs, reference to "an analyte" includes mixtures of analytes, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The term "microprocessor" refers to a computer processor contained on an integrated circuit chip, such a processor may also include memory and associated circuits. A microprocessor may further comprise programmed instructions to execute or control selected functions, computational methods, switching, etc. Microprocessors and associated devices are commercially available from a number of sources, including, but not limited to, Cypress Semiconductor Corporation, San Jose, Calif.; IBM Corporation, White Plains, N.Y.; Applied Microsystems Corporation, Redmond, Wash.; Intel Corporation, Chandler, Ariz.; and, National Semiconductor, Santa Clara, Calif.

The terms "analyte" and "target analyte" are used to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device," "sampling mechanism" or "sampling system" refers to any device and/or associated method for obtaining a sample from a biological system for the purpose of determining the concentration of an analyte of interest. Such "biological systems" include any biological system from which the analyte of interest can be extracted, including, but not limited to, blood, interstitial fluid, perspiration and tears. Further, a "biological system" includes both living and artificially maintained systems. The term "sampling" mechanism refers to extraction of a substance from the biological system, generally across a membrane such as the stratum corneum or mucosal membranes, wherein said sampling is invasive, minimally invasive, semi-invasive or non-invasive. The membrane can be natural or artificial, and can be of plant or animal nature, such as natural or artificial skin, blood vessel tissue, intestinal tissue, and the like. Typically, the sampling mechanism is in operative contact with a "reservoir," or "collection reservoir," wherein the sampling mechanism is used for extracting the analyte from the biological system into the reservoir to obtain the analyte in the reservoir. Non-limiting examples of sampling techniques include iontophoresis, sonophoresis (see, e.g., International Publication No. WO 91/12772, published 5 Sep. 1991; U.S. Pat. No. 5,636,632), suction, electroporation, thermal poration, passive diffusion (see, e.g., International Publication Nos.: WO 97/38126 (published 16 Oct. 1997); WO 97/42888, WO 97/42886, WO 97/42885, and WO 97/42882 (all published 20 Nov. 1997); and WO 97/43962 (published 27 Nov. 1997)), microfine (miniature) lances or cannulas, biolistic (e.g., using particles accelerated to high speeds), subcutaneous implants or insertions, and laser devices (see, e.g., Jacques et al. (1978) J. Invest. Dermatology 88:88–93; International Publication WO 99/44507, published 1999 Sep. 10; International Publication WO 99/44638, published 1999 Sep. 10; and International Publication WO 99/40848, published 1999 Aug. 19). Iontophoretic sampling devices are described, for example, in International Publication No. WO 97/24059, published 10 Jul. 1997; European Patent Application EP 0942 278, published 15 Sep. 1999; International Publication No. WO 96/00110, published 4 Jan. 1996; International Publication No. WO 97/10499, published 2 Mar. 1997; U.S. Pat. Nos. 5,279,543; 5,362,307; 5,730,714; 5,771,890; 5,989,409; 5,735,273; 5,827,183; 5,954,685 and 6,023,629, all of which are herein incorporated by reference in their entireties. Further, a polymeric membrane may be used at, for example, the electrode surface to block or inhibit access of interfering species to the reactive surface of the electrode.

The term "physiological fluid" refers to any desired fluid to be sampled, and includes, but is not limited to, blood, cerebrospinal fluid, interstitial fluid, semen, sweat, saliva, urine and the like.

The term "artificial membrane" or "artificial surface," refers to, for example, a polymeric membrane, or an aggregation of cells of monolayer thickness or greater which are grown or cultured in vivo or in vitro, wherein said membrane or surface functions as a tissue of an organism but is not actually derived, or excised, from a pre-existing source or host.

A "monitoring system" or "analyte monitoring device" refer to a system useful for obtaining frequent measurements of a physiological analyte present in a biological system. Such a device is useful, for example, for monitoring the amount or concentration of an analyte in a subject. Such a system may comprise, but is not limited to, a sampling mechanism, a sensing mechanism, and a microprocessor mechanism in operative communication with the sampling mechanism and the sensing mechanism. Such a device typically provides frequent measurement or determination of analyte amount or concentration in the subject and provides an alert or alerts when levels of the analyte being monitored fall outside of a predetermined range. Such devices may comprise durable and consumable (or disposable) elements. The term "glucose monitoring device" refers to a device for monitoring the amount or concentration of glucose in a subject. Such a device typically provides a frequent measurement or determination of glucose amount or concentration in the subject and provides an alert or alerts when glucose levels fall outside of a predetermined range. One such exemplary glucose monitoring device is the GlucoWatch® (Cygnus, Inc., Redwood City, Calif., US) biographer. The GlucoWatch biographer comprises two primary elements, a durable element (comprising a watch-type housing, circuitry, display element, microprocessor element, electrical connector elements, and may further comprise a power supply) and a consumable, or disposable, element (e.g., an AutoSensor component involved in sampling and signal detection, see, for example, WO 99/58190, published 18 Nov. 1999). This and similar devices is described, for example, in the following publications: Tamada, et al., (1999) *JAMA* 282:1839–1844; U.S. Pat. No. 5,771,890, issued 30 Jun. 1998; U.S. Pat. No. 5,735,273, issued 7 Apr. 1998; U.S. Pat. No. 5,827,183, issued 27 Oct. 1998; U.S. Pat. No. 5,954,685, issued 21 Sep. 1999; U.S. Pat. No. 5,989,409, issued 23 Nov. 1999; U.S. Pat. No. 6,023,629, issued 8 Feb. 2000; EP Patent Application EP 0 942 278 A2, published 15 Sep. 1999; PCT International Application WO 96/001100, published 4 Jan. 1996; PCT International Application WO 99/58190, published 18 Nov. 1999. The GlucoWatch biographer provides a device for frequent sampling of glucose from a subject the application of low intensity electric fields across the skin (iontophoresis) to enhance the transport of glucose from body tissues to a sampling chamber. In addition, when the concentration or amount of glucose has been determined to be outside of a predetermined range of values (or monitored glucose in the subject falls too quickly) the GlucoWatch biographer produces an alert or alarm signal. Such an alert or alarm is a component of the GlucoWatch biographer.

A "measurement cycle" typically comprises extraction of an analyte from a subject, using, for example, a sampling device, and sensing of the extracted analyte, for example, using a sensing device, to provide a measured signal, for example, a measured signal response curve. A complete measurement cycle may comprise one or more sets of extraction and sensing.

The term "frequent measurement" refers to a series of two or more measurements obtained from a particular biological system, which measurements are obtained using a single device maintained in operative contact with the biological system over a time period in which a series of measurements (e.g., second, minute or hour intervals) is obtained. The term thus includes continual and continuous measurements.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female.

The term "transdermal" includes both transdermal and transmucosal techniques, i.e., extraction of a target analyte across skin, e.g., stratum corneum, or mucosal tissue. Aspects of the invention which are described herein in the context of "transdermal," unless otherwise specified, are meant to apply to both transdermal and transmucosal techniques.

The term "transdermal extraction," or "transdermally extracted" refers to any sampling method, which entails extracting and/or transporting an analyte from beneath a tissue surface across skin or mucosal tissue. The term thus includes extraction of an analyte using, for example, iontophoresis (reverse iontophoresis), electroosmosis, sonophoresis, microdialysis, suction, and passive diffusion. These methods can, of course, be coupled with application of skin penetration enhancers or skin permeability enhancing technique such as various substances or physical methods such as tape stripping or pricking with micro-needles. The term "transdermally extracted" also encompasses extraction techniques which employ thermal poration, laser microporation, electroporation, microfine lances, microfine cannulas, subcutaneous implants or insertions, combinations thereof, and the like.

The term "iontophoresis" refers to a method for transporting substances across tissue by way of an application of electrical energy to the tissue. In conventional iontophoresis, a reservoir is provided at the tissue surface to serve as a container of (or to provide containment for) material to be transported Iontophoresis can be carried out using standard methods known to those of skill in the art, for example by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode). For example, see U.S. Pat. Nos. 5,771,890 and 6,023,629 and PCT Publication No. WO 96/00109, published 4 Jan. 1996.

The term "reverse iontophoresis" refers to the movement of a substance from a biological fluid across a membrane by way of an applied electric potential or current. In reverse iontophoresis, a reservoir is provided at the tissue surface to receive the extracted material, as used in the GlucoWatch biographer glucose monitor (Cygnus, Inc., Redwood City, Calif.; see, e.g., Tamada et al. (1999) JAMA 282:1839–1844).

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," or "sensing mechanism," encompasses any device that can be used to measure the concentration or amount of an analyte, or derivative thereof, of interest. Preferred sensing devices for detecting blood analytes generally include electrochemical devices, optical and chemical devices and combinations thereof. Examples of electrochemical devices include the Clark electrode system (see, e.g., Updike, et al., (1967) Nature 214:986–988), and other amperometric, coulometric, or potentiometric electrochemical devices, as well as, optical methods, for example UV detection or infrared detection (e.g., U.S. Pat. No. 5,747,806).

A "biosensor" or "biosensor device" includes, but is not limited to, a "sensor element" that includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, and silver, as well as, oxides, and dioxides, thereof, and combinations or alloys of the foregoing, which may include carbon as well. Some catalytic materials, membranes, and fabrication technologies suitable for the construction of amperometric biosensors are described by Newman, J. D., et al. (1995) Analytical Chemistry 67:4594–4599.

The "sensor element" can include components in addition to the sensing electrode, for example, it can include a "reference electrode" and a "counter electrode." The term "reference electrode" is used to mean an electrode that provides a reference potential, e.g., a potential can be established between a reference electrode and a working electrode. The term "counter electrode" is used to mean an electrode in an electrochemical circuit that acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are preferred.

In one embodiment, the "counter electrode" of the "sensor element" comprises a "bimodal electrode." The term "bimodal electrode" typically refers to an electrode which is capable of functioning non-simultaneously as, for example, both the counter electrode (of the "sensor element") and the iontophoretic electrode (of the "sampling mechanism") as described, for example, U.S. Pat. No. 5,954,685.

The terms "reactive surface," and "reactive face" are used interchangeably herein to mean the surface of the sensing electrode that: (1) is in contact with the surface of an ionically conductive material which contains an analyte or through which an analyte, or a derivative thereof, flows from a source thereof; (2) is comprised of a catalytic material (e.g., a platinum group metal, platinum, palladium, rhodium, ruthenium, or nickel and/or oxides, dioxides and combinations or alloys thereof) or a material that provides sites for electrochemical reaction; (3) converts a chemical signal (for example, hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

An "ionically conductive material" refers to any material that provides ionic conductivity, and through which electrochemically active species can diffuse. The ionically conductive material can be, for example, a solid, liquid, or semisolid (e.g., in the form of a gel) material that contains an electrolyte, which can be composed primarily of water and ions (e.g., sodium chloride), and generally comprises 50% or more water by weight. The material can be in the form of a hydrogel, a sponge or pad (e.g., soaked with an electrolytic solution), or any other material that can contain an electrolyte and allow passage of electrochemically active species, especially the analyte of interest. Some exemplary hydrogel formulations are described in WO 97/02811, published Jan. 30, 1997. The ionically conductive material may comprise a biocide. For example, during manufacture of an AutoSensor assembly, one or more biocides may be incorporated into the ionically conductive material. Biocides of interest include, but are not limited to, compounds such as chlorinated hydrocarbons; organometallics; hydrogen releasing compounds; metallic salts; organic sulfur compounds; phenolic compounds (including, but not limited to, a variety of Nipa Hardwicke Inc. liquid preservatives registered under the trade names Nipastat®, Nipaguard®, Phenosept®, Phenonip®, Phenoxetol®, and Nipacide®); quaternary ammonium compounds; surfactants and other membrane-disrupting agents (including, but not limited to, undecylenic acid and its salts), combinations thereof, and the like.

The term "buffer" refers to one or more components which are added to a composition in order to adjust or maintain the pH of the composition.

The term "electrolyte" refers to a component of the ionically conductive medium which allows an ionic current to flow within the medium. This component of the ionically conductive medium can be one or more salts or buffer components, but is not limited to these materials.

The term "collection reservoir" is used to describe any suitable containment method or device for containing a sample extracted from a biological system. For example, the collection reservoir can be a receptacle containing a material which is ionically conductive (e.g., water with ions therein), or alternatively it can be a material, such as a sponge-like material or hydrophilic polymer, used to keep the water in place. Such collection reservoirs can be in the form of a hydrogel (for example, in the shape of a disk or pad). Hydrogels are typically referred to as "collection inserts." Other suitable collection reservoirs include, but are not limited to, tubes, vials, strips, capillary collection devices, cannulas, and miniaturized etched, ablated or molded flow paths.

A "collection insert layer" is a layer of an assembly or laminate comprising a collection reservoir (or collection insert) located, for example, between a mask layer and a retaining layer.

A "laminate" refers to structures comprised of, at least, two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, chemical compounds such as, cyanoacrylate adhesives, and epoxies, as well as adhesives having such physical attributes as, but not limited to, the following: pressure sensitive adhesives, thermoset adhesives, contact adhesives, and heat sensitive adhesives.

A "collection assembly" refers to structures comprised of several layers, where the assembly includes at least one collection insert layer, for example a hydrogel. An example of a collection assembly as referred to in the present invention is a mask layer, collection insert layer, and a retaining layer where the layers are held in appropriate functional relationship to each other but are not necessarily a laminate (i.e., the layers may not be bonded together. The layers may, for example, be held together by interlocking geometry or friction).

The term "mask layer" refers to a component of a collection assembly that is substantially planar and typically contacts both the biological system and the collection insert layer. See, for example, U.S. Pat. Nos. 5,735,273, 5,827,183, and 6,201,979, all herein incorporated by reference.

The term "gel retaining layer" or "gel retainer" refers to a component of a collection assembly that is substantially planar and typically contacts both the collection insert layer and the electrode assembly.

The term "support tray" typically refers to a rigid, substantially planar platform and is used to support and/or align the electrode assembly and the collection assembly. The support tray provides one way of placing the electrode assembly and the collection assembly into the sampling system.

An "AutoSensor assembly" refers to a structure generally comprising a mask layer, collection insert layer, a gel retaining layer, an electrode assembly, and a support tray. The AutoSensor assembly may also include liners where the layers are held in approximate, functional relationship to each other. Exemplary collection assemblies and AutoSensor structures are described, for example, in International Publication WO 99/58190, published 18 Nov. 1999; and U.S. Pat. Nos. 5,735,273 and 5,827,183. The mask and retaining layers are preferably composed of materials that are substantially impermeable to the analyte (chemical signal) to be detected; however, the material can be permeable to other substances. By "substantially impermeable" is meant that the material reduces or eliminates chemical signal transport (e.g., by diffusion). The material can allow for a low level of chemical signal transport, with the proviso that chemical signal passing through the material does not cause significant edge effects at the sensing electrode.

The terms "about" or "approximately" when associated with a numeric value refers to that numeric value plus or minus 10 units of measure (i.e. percent, grams, degrees or volts), preferably plus or minus 5 units of measure, more preferably plus or minus 2 units of measure, most preferably plus or minus 1 unit of measure.

By the term "printed" is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, electroplating, laminating, or the like.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

"Parameter" refers to an arbitrary constant or variable so appearing in a mathematical expression that changing it give various cases of the phenomenon represented (McGraw-Hill Dictionary of Scientific and Technical Terms, S. P. Parker, ed., Fifth Edition, McGraw-Hill Inc., 1994). In the context of the GlucoWatch biographer, a parameter is a variable that influences the value of the blood glucose level as calculated by an algorithm.

"Decay" refers to a gradual reduction in the magnitude of a quantity, for example, a current detected using a sensor electrode where the current is correlated to the concentration of a particular analyte and where the detected current gradually reduces but the concentration of the analyte does not.

The terms "disease state," "condition" and "medical condition" refer to any physiological or environmental state about which a subject has concern. Exemplary disease states and conditions are described extensively herein, for example hypogylcemia, hyperglycemia, cardiovascular disease, cystic fibrosis, gestational diabetes, weight management regime, cancer remission, *Candida* infection, human immunodeficiency virus (HIV) infection, long distance driving, organ transplants recipients, subjects receiving growth hormone therapy, renal failure patients, malaria infection, alcoholism, etc.

2. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2.1.1 Exemplary Monitoring Systems

Numerous analyte monitoring systems can be used in the practice of the present invention. Typically, the monitoring system used to monitor the level of a selected analyte in a target system comprises a sampling device, which provides a sample comprising the analyte, and a sensing device, which detects the amount or concentration of the analyte or a signal associated with the analyte amount or concentration in the sample.

One exemplary monitoring system (the GlucoWatch biographer) is described herein for monitoring glucose levels in a biological system via the transdermal extraction of glucose from the biological system, particularly an animal subject, and then detection of signal corresponding to the amount or concentration of the extracted glucose. Transdermal extraction is carried out by applying an electrical current or ultrasonic radiation to a tissue surface at a collection site. The electrical current is used to extract small amounts of glucose from the subject into a collection reservoir. The collection reservoir is in contact with a sensor element (e.g., a biosensor) which provides for measurement of glucose concentration in the subject. As glucose is transdermally extracted into the collection reservoir, the analyte reacts with the glucose oxidase within the reservoir to produce hydrogen peroxide. The presence of hydrogen peroxide generates a current at the biosensor electrode that is directly proportional to the amount of hydrogen peroxide in the reservoir. This current provides a signal which can be detected and interpreted (for example, employing a selected algorithm) by an associated system controller to provide a glucose concentration value or amount for display.

In the use of the sampling system, a collection reservoir is contacted with a tissue surface, for example, on the stratum corneum of a subject's skin. An electrical current is then applied to the tissue surface in order to extract glucose from the tissue into the collection reservoir. Extraction is carried out, for example, frequently over a selected period of time. The collection reservoir is analyzed, at least periodically and typically frequently, to measure glucose concentration therein. The measured value correlates with the subject's blood glucose level.

To sample the analyte, one or more collection reservoirs are placed in contact with a tissue surface on a subject. The ionically conductive material within the collection reservoir is also in contact with an electrode (for reverse iontophoretic extraction) which generates a current sufficient to extract glucose from the tissue into the collection reservoir. Referring to FIG. 1, an exploded view of exemplary components comprising one embodiment of an AutoSensor for use in an iontophoretic sampling system is presented. The AutoSensor components include two biosensor/iontophoretic electrode assemblies, 104 and 106, each of which have an annular iontophoretic electrode, respectively indicated at 108 and 110, which encircles a biosensor electrode 112 and 114. The electrode assemblies 104 and 106 are printed onto a polymeric substrate 116 which is maintained within a sensor tray 118. A collection reservoir assembly 120 is arranged over the electrode assemblies, wherein the collection reservoir assembly comprises two hydrogel inserts 122 and 124 retained by a gel retaining layer 126 and mask layer 128. Further release liners may be included in the assembly, for example, a patient liner 130, and a plow-fold liner 132. In one embodiment, the electrode assemblies include bimodal electrodes. A mask layer 128 (for example, as described in PCT Publication No. WO 97/10356, published 20 Mar. 1997, and U.S. Pat. Nos. 5,735,273, 5,827,183, 6,141,573, and 6,201,979, all herein incorporated by reference) may be present. Other AutoSensor embodiments are described in WO 99/58190, published 18 Nov. 1999, herein incorporated by reference.

The mask and retaining layers are preferably composed of materials that are substantially impermeable to the analyte (e.g., glucose) to be detected (see, for example, U.S. Pat. Nos. 5,735,273, and 5,827,183, both herein incorporated by reference). By "substantially impermeable" is meant that the material reduces or eliminates analyte transport (e.g., by diffusion). The material can allow for a low level of analyte transport, with the proviso that the analyte that passes through the material does not cause significant edge effects at the sensing electrode used in conjunction with the mask and retaining layers. Examples of materials that can be used to form the layers include, but are not limited to, polyester, polyester derivatives, other polyester-like materials, polyurethane, polyurethane derivatives and other polyurethane-like materials.

The components shown in exploded view in FIG. 1 (i.e., an exemplary AutoSensor) are intended for use in a automatic sampling system which is configured to be worn like an ordinary wristwatch, as described, for example, in PCT Publication No. WO 96/00110, published 4 Jan. 1996, herein incorporated by reference. The AutoSensor in this case is a consumable element. A durable element, that is the wristwatch housing into which the AutoSensor is inserted, is also provided. The durable element can further include suitable electronics (e.g., one or more microprocessor(s), memory, display and other circuit components) and power sources, for example, for operating the automatic sampling system. The durable element also provides means to provide an audible alert when glucose levels in a subject being monitored are outside of a predetermined range. Further, such a device may also provide an audible alert when a trend is identified (for example, using an algorithm, e.g., U.S. Pat. No. 6,233,471, issued 15 May 2001) that indicates that glucose levels are dropping too quickly or increasing too quickly. For example, the GlucoWatch biographer provides an alert when glucose levels are falling faster than a predetermined rate. The one or more microprocessors may control a variety of functions, including, but not limited to, control of a sampling device, a sensing device, aspects of the measurement cycle (for example, timing of sampling and sensing, and alternating polarity between electrodes), connectivity, computational methods, different aspects of data manipulation (for example, acquisition, recording, recalling, comparing, and reporting), etc.

The sensing electrode can be, for example, a Pt-comprising electrode configured to provide a geometric surface area of about 0.1 to 3 cm$^2$, preferably about 0.5 to 2 cm$^2$, and more preferably about 1 cm$^2$. This particular configuration is scaled in proportion to the collection area of the collection reservoir used in the sampling system of the present invention, throughout which the extracted analyte and/or its reaction products will be present. The electrode composition is formulated using analytical- or electronic-grade reagents and solvents which ensure that electrochemical and/or other residual contaminants are avoided in the final composition, significantly reducing the background noise inherent in the resultant electrode. In particular, the reagents and solvents used in the formulation of the electrode are selected so as to be substantially free of electrochemically active contaminants (e.g., anti-oxidants), and the solvents in particular are selected for high volatility in order to reduce washing and cure times. Some electrode embodiments are described in European Patent Publication 0 942 278 A2, published Sep. 15, 1999, herein incorporated by reference.

The reactive surface of the sensing electrode can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al. (Analytical Chemistry 67(24), 4594–4599, 1995, herein incorporated by reference).

Any suitable iontophoretic electrode system can be employed, an exemplary system uses a silver/silver chloride (Ag/AgCl) electrode system. The iontophoretic electrodes are formulated typically using two performance criteria: (1) the electrodes are capable of operation for extended periods, preferably periods of up to 24 hours or longer; and (2) the electrodes are formulated to have high electrochemical purity in order to operate within the present system which requires extremely low background noise levels. The electrodes must also be capable of passing a large amount of charge over the life of the electrodes. With regard to operation for extended periods of time, Ag/AgCl electrodes are capable of repeatedly forming a reversible couple which operates without unwanted electrochemical side reactions (which could give rise to changes in pH, and liberation of hydrogen and oxygen due to water hydrolysis). The Ag/AgCl electrode is thus formulated to withstand repeated cycles of current passage in the range of about 0.01 to 1.0 mA per cm$^2$ of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also typically formulated using analytical- or electronic-grade reagents and solvents, and the polymer binder composition is selected to be free of electrochemically active contaminants which could diffuse to the biosensor to produce a background current.

The automatic sampling system can transdermally extract the sample over the course of a selected period of time using reverse iontophoresis. The collection reservoir comprises an ionically conductive medium, preferably the hydrogel medium described hereinabove. A first iontophoresis electrode is contacted with the collection reservoir (which is typically in contact with a target, subject tissue surface), and a second iontophoresis electrode is contacted with either a second collection reservoir in contact with the tissue surface, or some other ionically conductive medium in contact with the tissue. A power source provides an electrical potential between the two electrodes to perform reverse iontophoresis in a manner known in the art. As discussed above, the biosensor selected to detect the presence, and possibly the level, of the target analyte (for example, glucose) within a reservoir is also in contact with the reservoir. Typically, there are two collections reservoirs, each comprising glucose oxidase, and each in operative contact with iontophoretic electrode and a sensing electrode. The iontophoretic electrode may be a bimodal electrode that also serves, non-concurrently, as a counter electrode to the sensing electrode (see, for example, U.S. Pat. No. 5,954,685, herein incorporated by reference).

In practice, an electric potential (either direct current or a more complex waveform) is applied between the two iontophoresis electrodes such that current flows from the first electrode through the first conductive medium into the skin, and back out from the skin through the second conductive medium to the second electrode. This current flow extracts substances through the skin into the one or more collection reservoirs through the process of reverse iontophoresis or electroosmosis. The electric potential may be applied as described in PCT Publication No. WO 96/00110, published 4 Jan. 1996, herein incorporated by reference. Typically, the electrical potential is alternated between two reservoirs to provide extraction of analyte into each reservoir in an alternating fashion (see, for example, U.S. Pat. Nos. 6,023,629, 5,954,685, both herein incorporated by reference). Analyte is also typically detected in each reservoir.

As an example, to extract glucose, the applied electrical current density on the skin or tissue can be in the range of about 0.01 to about 2 mA/cm$^2$. In order to facilitate the extraction of glucose, electrical energy can be applied to the electrodes, and the polarity of the electrodes can be, for example, alternated so that each electrode is alternately a cathode or an anode. The polarity switching can be manual or automatic. A device and method for sampling of substances using alternating polarity is described in U.S. Pat. No. 5,771,890, issued Jun. 30, 1998, herein incorporated by reference.

When a bimodal electrode is used (e.g., U.S. Pat. No. 5,954,685, issued Sep. 21, 1999, herein incorporated by reference), during the reverse iontophoretic phase, a power source provides a current flow to the first bimodal electrode to facilitate the extraction of the chemical signal into the reservoir. During the sensing phase, a separate power source is used to provide voltage to the first sensing electrode to drive the conversion of chemical signal retained in reservoir to electrical signal at the catalytic face of the sensing electrode. The separate power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode subassembly can be operated by electrically connecting the bimodal electrodes such that each electrode is capable of functioning as both an iontophoretic electrode and counter electrode along with appropriate sensing electrode(s) and reference electrode(s).

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present invention, the electrical current measured at the sensing electrode subassembly is the current that is correlated with an amount of chemical signal corresponding to the analyte.

The detected current can be correlated with the subject's blood glucose concentration (e.g., using a statistical technique or algorithm or combination of techniques) so that the system controller may display the subject's actual blood glucose concentration as measured by the sampling system. Such statistical techniques can be formulated as algorithm(s) and incorporated in one or more microprocessor(s) associated with the sampling system. Exemplary signal processing applications include, but are not limited to, those taught in the following U.S. Pat. Nos. 6,144,869, 6,233,471, 6,180,416, herein incorporated by reference.

In a further aspect of the present invention, the sampling/sensing mechanism and user interface may be found on separate components. Thus, the monitoring system can comprise at least two components, in which a first component comprises sampling mechanism and sensing mechanism that are used to extract and detect an analyte, for example, glucose, and a second component that receives the analyte data from the first component, conducts data processing on the analyte data to determine an analyte concentration and then displays the analyte concentration data. Typically, microprocessor functions (e.g., control of a sampling device, a sensing device, aspects of the measurement cycle, computational methods, different aspects of data manipulation or recording, etc.) are found in both components. Alternatively, microprocessing components may be located in one or the other of the at least two components. The second component of the monitoring system can assume many forms, including, but not limited to, the following: a watch, a credit card-shaped device (e.g., a "smart card" or "universal card" having a built-in microprocessor as described for example in U.S. Pat. No. 5,892,661, herein incorporated by reference), a pager-like device, cell phone-like device, or other such device that communicates information to the user visually, audibly, or kinesthetically.

Further, additional components may be added to the system, for example, a third component comprising a display of analyte values or an alarm related to analyte concentration, may be employed. In certain embodiments, a delivery unit is included in the system. An exemplary delivery unit is an insulin delivery unit. Insulin delivery units, both implantable and external, are known in the art and described, for example, in U.S. Pat. Nos. 5,995,860; 5,112,614 and 5,062,841, herein incorporated by reference. Preferably, when included as a component of the present invention, the delivery unit is in communication (e.g., wire-like or wireless communication) with the extracting and/or sensing mechanism such that the sensing mechanism can control the insulin pump and regulate delivery of a suitable amount of insulin to the subject.

Advantages of separating the first component (e.g., including the biosensor and iontophoresis functions) from the second component (e.g., including some microprocessor and display functions) include greater flexibility, discretion, privacy and convenience to the user. Having a small and lightweight measurement unit allows placement of the two components of the system on a wider range of body sites, for example, the first component may be placed on the abdomen or upper arm. This wider range of placement options may improve the accuracy through optimal extraction site selection (e.g., torso rather than extremities) and greater temperature stability (e.g., via the insulating effects of clothing). Thus, the collection and sensing assembly will be able to be placed on a greater range of body sites. Similarly, a smaller and less obtrusive microprocessor and display unit (the second component) provides a convenient and discrete system by which to monitor analytes. The biosensor readouts and control signals will be relayed via wire-like or wireless technology between the collection and sensing assembly and the display unit which could take the form of a small watch, a pager, or a credit card-sized device. This system also provides the ability to relay an alert message or signal during nighttime use, for example, to a site remote from the subject being monitored.

In one embodiment, the two components of the device can be in operative communication via a wire or cable-like connection. Operative communications between the components can be wireless link, i.e. provided by a "virtual cable," for example, a telemetry link. This wireless link can be uni- or bi-directional between the two components. In the case of more than two components, links can be a combination of wire-like and wireless.

2.1.2 Exemplary Analytes

The analyte can be any one or more specific substance, component, or combinations thereof that one is desirous of detecting and/or measuring in a chemical, physical, enzymatic, or optical analysis.

Analytes that can be measured using the methods of the present invention include, but are not limited to, amino acids, enzyme substrates or products indicating a disease state or condition, other markers of disease states or conditions, drugs of abuse (e.g., ethanol, cocaine), therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate and/or lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. Analytes in non-biological systems may also be evaluated using the methods of the present invention.

In preferred embodiments, the analyte is a physiological analyte of interest, for example glucose, or a chemical that has a physiological action, for example a drug or pharmacological agent.

In order to facilitate detection of the analyte, an enzyme (or enzymes) can be disposed within the one or more collection reservoirs. The selected enzyme is capable of catalyzing a reaction with the extracted analyte to the extent that a product of this reaction can be sensed, e.g., can be detected electrochemically from the generation of a current which current is detectable and proportional to the amount of the analyte which is reacted. In one embodiment of the present invention, a suitable enzyme is glucose oxidase, which oxidizes glucose to gluconic acid and hydrogen peroxide. The subsequent detection of hydrogen peroxide on an appropriate biosensor electrode generates two electrons per hydrogen peroxide molecule creating a current that can be detected and related to the amount of glucose entering the device. Glucose oxidase (GOx) is readily available commercially and has well known catalytic characteristics. However, other enzymes can also be used singly (for detection of individual analytes) or together (for detection of multiple analytes), as long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, cholesterol with a cholesterol oxidase system, and theophylline with a xanthine oxidase system.

In addition, the oxidase enzyme (used for hydrogen peroxidase-based detection) can be replaced or complemented with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea.

Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytoin), chemotherapy (e.g., adriamycin), hyperactivity (e.g., ritalin), and anti-organ-rejection (e.g., cyclosporin).

Preferably, a sensor electrode is able to detect the analyte that has been extracted into the one or more collection reservoirs when present at nominal concentration levels. Suitable exemplary biosensor electrodes and associated sampling systems as described in are described in PCT Publication Nos. WO 97/10499, published 20 Mar. 1997 and WO 98/42252, published 1 Oct. 1998, both herein incorporated by reference herein.

A single sensor may detect multiple analytes and/or reaction products of analytes. For example, a platinum sensor could be used to detect tyrosine and glucose in a single sample. The tyrosine is detected, for example, by direct electrochemical oxidation at a suitable electrode potential (e.g., approximately 0.6V vs. Ag/AgCl). The glucose is detected, e.g., using glucose oxidase and detecting the hydrogen peroxide reaction product.

Different sensing devices and/or sensing systems can be employed as well to distinguish between signals. For example, a first gel containing glucose oxidase associated with a first platinum sensor can be used for the detection of glucose, while a second gel containing uricase associated with a second platinum sensor can be used for the detection of urea.

2.2.0 Applications of Frequent Analyte Monitoring

Many disease states and conditions will benefit from frequent monitoring of glucose and, optionally, one or more additional analytes. Non-limiting examples of such disease states and conditions that will benefit from frequent monitoring of glucose levels, include hyperglycemia; hypoglycemia; cystic fibrosis; AIDS; organic and amino acid disorders; cancer remission; as well as patients with cardiovascular disease; stroke patients; gestational diabetes; organ transplant recipients; those infected with *Candida*, HIV or malaria; elderly patients; kidney patients; young children; long-distance drivers; intense exercisers; subjects on a weight loss program or other special diet; subjects receiving growth hormone; and alcoholics. Furthermore, monitoring of glucose levels will also be beneficial in determining the effects of one or more pharmaceutical compositions on glucose levels or concentrations in a biological subject. In the present invention, at least one of the pharmaceutical compositions whose effect on glucose levels is monitored does not contain insulin.

2.2.1 Hyperglycemia

Hyperglycemia refers to excessive levels of blood glucose in a subject. The primary form of hyperglycemia is diabetes mellitus (DM), which is hyperglycemia secondary to decreased insulin where either production of insulin is decreased or peripheral tissue resistance to insulin is increased. Insulin-dependent DM (IDDM, or type I DM) accounts for about 10% of DM cases and usually occurs in childhood or early adulthood. Type I DM can result in ketoacidosis when patients are without insulin therapy. Non-insulin dependent DM (NIDDM, or type II DM) usually occurs in people >40 years of age, and about 60% of the patients are obese. Type II DM can also occur in animals, for example, domestic cats. These patients are not prone to ketosis but may develop it under conditions of stress. Gestational onset DM (GODM) occurs when diabetes onset is during pregnancy and resolves with delivery. These patients are at a higher risk for developing DM at a later date. Secondary DM can be caused, for example, by steroid therapy, Cushing's syndrome, pancreatectomy, pancreatic insufficiency secondary to pancreatitis, or endocrine disorders. The Diabetes Control and Complications Trial Group reported that the long-term complications of DM appear to be directly related to control of blood glucose levels. Thus, the conclusion of the study was that intensive therapy delays the onset and slows the progression of diabetic retinopathy, nephropathy, and neuropathy in patients with IDDM. Other studies have shown the same conclusions in NIDDM. Thus, frequent monitoring of blood glucose levels is an important tool for both diagnosing and determining appropriate therapy for many conditions associated with abnormal glucose levels.

2.2.1.1. Dysglycemia and Cardiovascular Disease

Recent research has found a connection between dysglycemia, or abnormal glucose levels, and risk factors (e.g., atherosclerosis and hypertension) for cardiovascular disease (see, for example, Gerstein H C, Yusuf S (1996) *Lancet* 347(9006): 949–950; Gerstein H C, Yusuf S (1998) *Diabetes Research and Clinical Practice* 40 Suppl: S9–S14; Meigs J B, Nathan D M et al. (1998) *Ann Intern Med* 128(7): 524–533; Tsai S T, Li C L et al. (2000) *J Clin Epidemiol.* 53(5): 505–510). For instance, atherosclerotic changes appear to develop in non-diabetic individuals with impaired glucose tolerance (see, e.g., Kawamori, R (1998) *Diabetes Res Clin Pract* 40 Suppl: S35–S42; Yamasaki Y, Kawamori R et al. (1995) *Diabetologia* 38(5):585–591). Similarly, hypertension is also associated with impaired glucose tolerance (Vaccaro et al. (1996) Diabetologia 39:70–76). At a molecular level, studies have shown a connection between a deletion polymorphism in the antigotensis-converting enzyme (ACE) gene (which is related to cardiovascular disease) and elevated plasma glucose levels after oral glucose load (Ohishi et al. (2000) *Clin Exp Pharmacol Physiol* 27:483–487). Further, high blood glucose concentration (in both diabetic and non-diabetic patients) increases the risk of death and poor outcome after acute myocardial infarction and significantly increases the mortality rate from cardiovascular disease (see, e.g., Capes et al. *Lancet* (2000) 355(9206):773–778; Feskens E J & Kromhout D (1992) *J Clin Epidemiol* 45(11): 1327–34 and Bjornholt et al. (1999) *Diabetes Care* 22(1): 45–49).

The risk of heart disease associated with hyperglycemia increases continuously across the spectrum of glucose tolerance categories, from those that are just barely above normal to those in the diabetic range. Generally speaking, as blood glucose levels increase, so does the likelihood that an individual will experience cardiovascular disease. (see, e.g., Temelkova-Kurktschiev et al. (2000) *Exp Clin Endocrinol Diabetes* 108:93–99). This relationship is similar to the relationship between smoking and blood pressure to cardiovascular risk.

Thus, monitoring and controlling blood glucose levels in individuals with a family or personal history of heart disease allows these subjects to reduce the risk of cardiovascular problems. Further, in certain embodiments, it will also be useful to monitor levels of glucose, cholesterol, triglycerides and/or therapeutic drugs used to treat high cholesterol, hypertension or the like.

2.2.1.2 Glucose Tolerance, Diabetes Onset and Cystic Fibrosis

It is estimated that approximately 50,000 individuals in the U.S. and Canada suffer from cystic fibrosis. One well-known complication of this disease is cystic fibrosis-related diabetes (CFRD) (Finkelstein S M & Wielinski C L (1988) *J Pediatr* 112(3): 373–377; Handwerger S, Roth J et al. (1969) *N Engl J Med* 281(9): 451–461). CFRD appears to be grossly underestimated in the U.S., probably due to the lack of routine oral glucose tolerance tests (see, e.g., Hardin D S & Moran A (1999) *Endocrinol Metab Clin North Am.* 28(4): 787–800). CFRD incidence has also increased as the life-spans of cystic fibrosis patients increase. In a 10 year study of CFRD, Cucinotta D, De Luca F et al. (1999) *Acta Paediatr* 88(4): 389–393 found that impaired glucose tolerance was the sole predictor of whether patients will develop CFRD.

Thus, frequent monitoring of blood glucose levels in cystic fibrosis patients will allow clinicians to detect diabetes earlier than was previously possible. Moreover, monitoring of trends in blood glucose levels can help identify groups who are prone to develop diabetes. In addition to monitoring glucose, the levels of chloride, sodium, and/or therapeutic drugs used to treat CF may also be monitored.

2.2.1.3 Abnormal Blood Glucose Levels in Stroke, Ischemia, Brain Injury, Head Injury, and Spinal Cord Injury Hyperglycemia following acute stroke is strongly associated with subsequent mortality, impaired neurological recovery and brain lesions in diabetic and non-diabetic patients (Sala et al. (1999) *Ann NY Acad Sci* 890:133–154; Weir C J, Murray G D et al. (1997) *BMJ* 314(7090): 1303–1306; Gray C S, Taylor R et al. (1987) *Diabet Med* 4(3): 237–40; Guyot et al. (2000) *Horm Metab Res.* 32:6–9; Hayahi (2000) *No To Hattatsu* 32:122–131; Rovlias and Kotsou (2000) *Neurosurgery* 46:335–342). Furthermore, between 20% and 50% of acute stroke patients are hyperglycemic at presentation. As a result, it is of increasing interest to study the effects of modulating blood glucose levels in stroke patients, for example by administering glucose potassium insulin (GKI) to these patients (Scott J F, Robinson G M et al. (1999) *Stroke* 30(4): 793–799; Scott J F, Gray C S et al. (1998) *QJ Med* 91(7): 511–515; Hennes et al. (1999) *Anaesthesist* 48:858–870; Schurr et al. (1999) *Ann NY Acad Sci* 893:386–390).

Thus, frequent monitoring blood glucose levels in stroke patients can allow clinicians to detect abnormal glucose levels at an early time and early treatment may reduce mortality and improve neurological outcomes.

2.2.1.4 Hyperglycemia Associated with Organ Transplantation

Impaired glucose tolerance or DM are also frequent complications after organ transplantation, in both human leukocyte antigen (HLA) matched and mismatched patients. For example, liver transplant recipients have been shown to have severe post-prandial hyperglycemia, which may be attributed to insulinpoenia and a late increased glucose turnover (Schneiter et al. (2000) *Diabetes Metab* 26:51–56; Petruzzo et al. (2000) *Diabetes Metab* 26:215–218). Similarly, in the context of grafts, Trick et al. (2000) *J Thorac Cardiovasc Surg* 119:108–114 report that appropriate control of preoperative blood glucose levels appears to help prevent deep sternal site infection after coronary artery bypass graft operations. Accordingly, frequent monitoring of blood glucose levels before and after transplant (e.g., organ transplant and grafts) is part of the present invention. Furthermore, multiple analytes in these subjects (e.g, glucose, an immunosuppressive drug, etc) can also be measured.

2.2.1.5 Hyperglycemia Associated with *Candida* Infection

Chronic or repeated infection with *Candida* (e.g., vulvovaginal candidiasis and congenital cutaneous candidiaseis in infants) is a widespread problem in both immunocompetent and immunosuppressed patients. A known etiology of recurrent candidiasis is hyperglycermia, see, e.g., Ringdahl (2000) *Am Fam Physician* 61:3306–3312. Further, because many patients experience recurrent *Candida* infections once prophylaxis is discontinued, long-term therapy may still be warranted. Therefore, frequent monitoring of blood glucose level is useful in subjects suffering from chronic or repeated infection with *Candida*.

2.2.1.6 Diet-Induced Hyperglycemia

Diet can also induce hyperglycemia in certain subjects. Diets high in carbohydrates and/or fat have been associated with development of insulin resistance and perturbed carbohydrate and lipid metabolism and leptin has been proposed as a treatment for diet induced hyperglycemia and insulin resistance (Buettner et al. (2000) *Am J Physiol Endocrinol Metab* 278: E563–9). Thus, in addition to allowing a subject to quickly and easily monitor blood glucose levels, the present invention allows for the monitoring of additional analytes, for example, leptin.

2.2.1.7 HIV-Related Hyperglycemia

The present invention will also find use in evaluating and determining treatment regimes for human immunodeficiency virus (HIV)-infected patients, particularly those patients currently receiving protease inhibitors. Although protease inhibitors have proven to be very useful in treating HIV infection in certain patients, these drugs often exhibit glucose-related side effects, including, for example, hyperglycemia, new-onset diabetes mellitus, lipodystrophic syndrome, central obesity, peripheral fat loss, and hyperlipidemia, Scevola et al. (2000) *AIDS Read* 10:365–369; 371–375; Mathe (1999) *Biomed Pharmacother* 53:449–451. Accordingly, all patients receiving protease inhibitors should be monitored for blood glucose levels.

2.2.1.8 Geriatric Hyperglycemia

The prevalence of hyperglycemia in elderly persons (e.g, greater than 60 years of age) is high and is significantly associated with cardiovascular risk factors such as obesity, high systolic pressure and hypertriglyceridemia, see, above and Lai et al. (2000) *J Gerontol A Biol Sci Med* 55:M255–256. Hyperglycemia is also more common elderly trauma patients and in those elderly patients exhibit hostility, Frankenfield et al. (2000) *J. Trauma* 48:49–56. Thus, is useful to monitor glucose levels in these in elderly patients.

2.2.1.9 Hyperglycemia in Neonates and Children

Transient hyperglycemia that occurs as a part of the stress response in acute illnesses can cause serious complications in infancy and childhood, Gupta et al. (1997) *Indian J Pediatr* 64:205–210. For example, non-ketotic hyperglycemia (NKH) in infancy and childhood can cause serious complications, for example, hydrocephalus requiring shunting and subsequent brain damage, Van Hove et al. (2000) *Neurol* 54:754–756. Thus, frequent monitoring of glucose (and, optionally, other analytes, such as ketones) is useful in young children.

Further, there are numerous reports of transient neonatal diabetes (Menon, P. S., et al., Indian J Pediatr 67(6):443–448, 2000; Shield, J. P., Horm Res 53(Suppl. 1): 7–11, 2000; Stanley, C. A., Pediatr Clin North Am 44(2): 363–374, 1997; Wilson, S., Nurs Times 87(36):44–45, 1991). There are numerous causes that are thought to contribute to such transient neonatal diabetes, including, but not limited to, chromosomal abnormality, genotypic effects, and/or imprinting (Varrault, A., et al., J Biol Chem 276(22) 18653–18656, 2001; Marquis, E., et al., Tissue Antigens 56(3):217–222, 2000; Gardner, R. J., et al., Hum Mol Genet 9(4):589–596, 2000; Kamiya, M., et al., Hum Mol Genet 9(3):453–460, 2000; Shield, J. P., et al., Arch Dis Child Fetal Neonatal Ed 76(1):F39–42, 1997), treatments (e.g., drug treatments to mother and/or neonate) (Moniaci, V. K., et al., J Perinat Neonatal Nurs 11 (4): 60–64, 1998; Uhrig, J. D., et al., Can Med Assoc J 128(4):368–371, 1983; Bomba-Opon, D. A., et al., Ginekol Pol 71(8):887–892, 2000; Yunis, K. A., et al., Am J Perinatol 16(1):17–21, 1999), nutrition (Barker, D. J., Nutrition 13(9):807–813, 1997), and disease states (e.g., in the mother and/or neonate) (Ahlfors, K., et al., Scand J Infect Dis. 31(5):443–457, 1999; Lorenzi, P., et al., AIDS, Dec. 24, 12(18):F241–247, 1998; Cooper, L. Z., Rev Infect Dis 7(Suppl. 1):S2–10, 1985). In addition, babies born before term may have glucose metabolism abnormalities (Gross, T. L., et al., Am J Obstet Gynecol 146(3):236–241, 1983; Lackman, F., Am J Obstet Gynecol 184(5):946–953, 2001).

Thus, frequent monitoring of glucose (and, optionally, other analytes, such as drug levels) is useful in neonates and premature neonates to reduce possible short- and/or long-term damage caused by low, high, or fluctuating glucose levels, as well as to increase probability of survival.

2.2.1.10 Hyperglycemia Associated with Intense Exercise

During intense exercise, fluctuations in the levels of various analytes, for example glucose, hormones, etc., has been shown to occur, Kreisman et al. (2000) *Am J Physiol Endocrinol Metab* 278:E7860793. Commonly, subjects who exercise intensely can become hyperglycemic. Marliss et al. (2000) *J Appl Physiol* 88:457–66. Accordingly, monitoring the level of glucose and/or other analytes such as hormones aids in regulating exercise intensity and/or intake of food or fluids during exercise.

2.2.2 Hypoglycemia

Hypoglycemia refers to decreased levels of glucose in plasma, or below normal levels. Although hypoglycemic subjects may be asymptomatic, many exhibit adrenergic stimulation symptoms including diaphoresis, anxiety, irritability, palpitations, tremor, and hunger. Hypoglycemic events may also occur during the night-time (nocturnal hypoglycemia), for example, when a person is sleeping, thus vulnerable to continuing decreases in levels of glucose in plasma. Severe hypoglycemia may cause confusion, visual blurring, loss of consciousness and seizures. Typically, hypoglycemia occurs about 2 to 4 hours postprandially and generally subsides in 15 to 20 minutes. The etiology of hypoglycemia is often idiopathic, but may be caused by early diabetes, malignancies of the pancreas, benign tumors of the pancreas, general hypertrophy of the pancreas without evident disease, alcohol intake and liver disease (decreased gluconeogenesis), gastrectomy, renal failure, drugs such as salicylates, beta-blockers, pentamidine, acetylcholine esterase (ACE) inhibitors, excess insulin including insulinoma, self-administered insulin or oral hypoglycemic agents; pituitary or adrenal insufficiency.

Clinicians are generally most concerned with functional or idiopathic hyperinsulinism, the most common type of which is caused by excessive intake of refined sugars, caffeine, emotional stress or a combination of these factors with sugar and caffeine compounded in their effects through a condition of stress. The Islets of Langerhans in the pancreas are over-stimulated by constant bombardment of refined sugar and caffeine producing greater amounts of insulin than required to metabolize the circulating blood sugar, thus keeping blood sugar levels lower than normal except for a very short time after ingestion of food. Eventually any sugar, good, bad, or indifferent, will trigger the pancreas to secrete excessive amounts of insulin. The liver is also heavily involved in this mechanism as it controls reconversion of stored glycogen into glucose for distribution in the blood stream. In addition, all the endocrine glands are linked in a dynamic balance to compensate for any deviation of blood sugar levels so that the brain and nervous system are never for an instant deprived of necessary amounts of blood sugar needed for their normal activity. This balance is upset by stress and symptoms such as anxiety, irritability, fear, sweating, flushing or pallor, numbness, chills, headaches, dizziness, weakness and faintness are common. However, the most obvious symptoms are excessive hunger just about all the time and great fatigue and weakness. Thus, hypoglycemia is an important medical issue and frequent monitoring of glucose levels is useful to a wide variety of subjects.

2.2.2.1 Hypoglycemia and Eating Disorders

Hypoglycemia can occur in individuals with anorexia nervosa (Alvin et al. (1993) *Arch Fr Pediatr* 50(9): 755–762; Ron Waldrop, M D "Anorexia Nervosa" From emedicine.com on the Internet and bulimia nervosa (Johnson et al. (1994) *Int J Eat Disord* 15(4): 331–341; Overduin J & Jansen A (1997) *Physiol Behav* 61(4): 569–575). In bulimic patients following purging of a meal, there is a dramatic reduction in insulin and glucose (Johnson et al., above). Because of the correlation between hypoglycemia and hunger, the hypoglycemia that results from purging may be partially responsible for continued binging and purging. Thus, monitoring blood glucose levels in patients with eating disorders can assist therapists in treating them, and can also help patients understand physiological processes that contribute to their problems.

2.2.2.2 Hypoglycemia and Pentamidine Therapy

Pentamidine is an effective agent for treating *Pneumocystis carinii* pneumonia in HIV-infected patients, the hemolymphatic stage of Gambian trypanosomiasis, and antimony-resistant leishmaniasis. Iatrogenic hypoglycemia occurs in one-quarter to one-third of HIV-infected patients treated with this drug, and it can become severe and even life-threatening, Andersen et al. (1986) *Drug Intell Clin Pharm* 20(11): 862–868; Stahl-Bayliss et al. (1986) *Clin Pharmacol Ther* 39(3): 271–5; Chan et al. (1996) *Drug Saf* 15(2): 135–157. Thus, frequent monitoring of the levels of blood glucose and, optionally, other analytes (e.g., pentadiene), in HIV-infected patients receiving pentamidine therapy will reduce the risk of nosocomial infections in them, and will reduce the risk of HIV transmission to needle-stick performing hospital personnel.

2.2.2.3 Hypoglycemia and Disease States

Many organic and amino acid disorders are also correlated with hypoglycemia, for example acidemias that involve the oxidation of fatty acids (Ozand et al. (2000) *Semin Perinatol* 24:172–193); Beckwith-Wiedemann syndrome (DeBaun et al. (2000) *Semin Perinatol* 24:164–171); glycogen storage diseases (Wolfsdorf et al. (1999) *Endocrinol Metab Clin North Am* 28:801–823; carbohydrate-deficient glycoprotein syndrome (Babovic-Vuksanovic et al. (1999) *J Pediatr* 135:775–781; hypopituitarism (Nanao et al. (1999) *Acta Paediatr* 88:1173; and mitochondrial respiratory chain disorders (Morris (1999) *Liver* 19:357–368).

Glycogen storage diseases (glycogenoses) are a group of hereditary disorders that result from a lack of at least one enzyme involved in glycogen synthesis or breakdown. The result is accumulation of glycogen in tissues. According to the Merck Manual (16$^{th}$ edition), hypoglycemia can be a severe problem in some of these glycogen storage diseases, for example, Type 0 (enzyme system affected, glycogen synthetase), Type Ia (enzyme system affected, glucose-6-phosphatase), Type Ib (enzyme system affected, glucose-6-phosphatase translocase), Type III (enzyme system affected, debrancher enzyme system), Type VI (enzyme system affected, liver phosphorylase). Patients with glycogen storage disorders must follow strict diets (in order to avoid hypoglycemia and other problems) and must monitor their blood glucose levels (see, Wolfsdorf, et al., above).

Thus, frequent monitoring of glucose levels non-invasively in these patients will likely improve their clinical outcomes and simplify their lives significantly.

2.2.2.4 Hypoglycemia and Alcoholism

Hypoglycemia is a common adverse effect of alcoholism, and it occurs in up to 95% of alcoholics, Bunout (1999) *Nutrition* 15(7–8): 583–589. Hypoglycemia due to excessive alcohol ingestion can be severe, and alcoholics are usually glucose intolerant as well, Kearney et al. (2000) *J R Soc Med* 93:15–17. This condition is most likely due to an inhibition of glucose-stimulated insulin secretion. Frequent, non-invasive monitoring of blood glucose levels and/or other analytes such as alcohol can treat alcoholics by allowing them to see clinical improvements in their blood sugar levels, or to allow them to see the extent to which alcohol abuse has damaged an important metabolic process.

2.2.2.5. Hypoglycemia and Long Distance Driving Performance

Long distance drivers often experience hypoglycemia. Further, the fatigue associated with hypoglycemia and the resulting possibility that these drivers may fall asleep at the wheel is a potential hazard, Frier (2000) *Diabetes Care* 23:148–150; Marrero et al. (2000) *Diabetes Care* 23:146–147. Long distance driving and associated risks are most frequently associated with long-haul trucker drivers (N Engl J Med. 1997 Sep. 11; 337(11):755–761). Long distance driving is, for example, sustained driving with little or no rest for 5 to 10 hours or more. Typical "long-haul" trucker drivers may drive from 10 to 15 hours at a time. The California Department of Motor Vehicles suggests a ten minute rest after even just two hours of driving. Frequent monitoring of glucose levels will allow long distance drivers to more adequately determine food and/or fluid intake. This in turn will decrease the risks posed by poor driving performance caused by hypoglycemia.

2.2.2.6 Hypoglycemia and Renal Failure

Hypoglycemia and its accompanying complications occur frequently in both diabetic and non-diabetic end stage renal failure (ESRF) patients, Haviv et al. (2000) *Ren Fail* 22:219–223. Accordingly, using the methods described herein, ESRF patients can benefit from frequent, periodic monitoring of glucose and/or other analyte levels (e.g., glucose and liver enzymes).

2.2.2.7 Hypoglycemia, Neonates, and Children

Hypoglycemia can cause severe problems in infants or children, including for example mild to severe brain damage (Kinnala et al. (2000) *Semin Perinatol* 24:116–119; Frey et al. (2000) *Scweiz Zmed Wochenschr* 130:151–155; Hawdon (1999) *Eur J Pediatr* 158 Suppl 1:S9–S12; see, also, Section 2.2.3 below). Because hypoglycemia can occur if feeding is postponed more than 12 to 24 hours post-partum, there remains a need for frequent and close clinical observation of neonates and other vulnerable children while avoiding excessively invasive management that may interfere with feeding. Thus, the present invention provides frequent monitoring of glucose levels and, optionally, the levels of other analytes which may signal neonatal distress, such as ketones.

2.2.2.8 Hypoglycemia and Growth Hormone Therapy

Growth hormone (GH) therapy has been recommended for short stature children and for hypoglycemias due to growth hormone deficiency. Increasingly, growth hormone therapy is also recommended for adults with growth hormone deficiency following pituitary tumor surgery or irradiation (Dash, et al., J. Assoc Physicians India 47:417–425, 1999). Further, the insulin tolerance test (ITT) is widely accepted as the method of choice to evaluate growth hormone secretion capacity in adults with hypothalamic-pituitary disorders, Hoeck, et al. (2000) *J Clin Endocrinol Metab* 85:1467–1472. Thus, the present invention can be used in both adults and children to monitor the levels of various analytes (e.g., glucose and/or growth hormone).

2.2.2.9 Hypoglycemia and Cancer Remission

Under most circumstances, tumors growth rapidly when the blood glucose supply is high and grow slowly when blood glucose supply is low. In cases of spontaneous remissions, tumors appear to grow rapidly and steadily despite low blood glucose and, consequently, the tumor system collapses and is removed by the immune system. It has been suggested that remission may be induced if hypoglycemia is initiated just prior to reducing the tumor mass and then maintaining the hypoglycemic state, Niakan (1999) *Cancer Biother Radiopharm* 14:297–298. In such regimes, the present invention can be used to monitor blood glucose levels to help the subject remain hypoglycemic during the critical period.

2.2.2.10 Hypoglycemia and Malaria

Severe malaria often presents with hypoglycemia, Agbenyega et al. (2000) *J Clin Endorcrinol Metab* 85:1569–1576. Furthermore, because hypoglycemia is a frequent complication of quinine therapy for malaria, frequent blood sugar estimations are required in treating malaria or quinine toxicity, Padmaja et al. (1999) *Indian J Med Sci* 53:153–157. Thus, the ability to monitor glucose and/or quinine levels is useful in relation to diagnosis and treatment of malaria.

2.2.2.11 Drug Treatment Related Hypoglycemia

As noted above, hypoglycemia is present in many diseases. One cause of hypoglycemia appears to be related to drug therapy, Virally et al. (1999) *Diabetes Metab* 25:477–490. For instance, saquinavir, a treatment for HIV, induces hypoglycemia in Type II diabetes (see, Zimhony and Stein (1999) *Ann Intern Med* 131:980), while indomethacin, a drug used to arteriosus in premature infants, also induces hypoglycemia. Consequently, frequent monitoring of analytes (e.g., glucose and/or the therapeutic drug) in these individuals is part of the present invention.

2.2.2.12 Hypoglycemia, Brain Injury and Stroke

As noted above, brain injury can be a serious complication of hypoglycemia de Courten-Meyers et al. (2000) *J Cereb Blood Flow Metab* 20:82–92; Losek (2000) *Ann Emerg Med* 35:43–46. There is also strong evidence that severe hypoglycemia can worsen the prognosis in acute stroke. Nagi et al. (1999) *Nervenarzt* 70:944–949. To determine appropriate treatment options, routine and rapid assessment of analytes such as glucose is recommended.

2.2.2.13 Hypoglycemia and Endurance Exercise and Training

Performance in endurance events requires an adequate supply of nutrients such as glucose. Thus, performance is optimized when training includes monitoring of glucose and other analyte levels combined with nutritional supplementation to prevent hypoglycemia, Coyle (1999) *J Sci Med Sport* 2:181–189.

2.2.2.14 Severe Hypoglycemia

Some individuals may experience recurrent bouts of severe hypoglycemia. Because such episodes of hypoglycemia may cause severe complications, it is recommended that individuals with a recent history of severe hypoglycemia better recognize the occurrence of low blood glucose. Cox et al. (1999) *Diabetes Care* 22:2018–2025. The present invention provides a fast and efficient way for these individuals to monitor glucose levels.

2.2.3 Pregnancy and Gestational Diabetes

Dysglycemia during pregnancy can cause severe problems for both mother and fetus, see, e.g., Schafer-Graft et al. (1999) *Ther Umsch* 56:572–576. For diabetic mothers who become pregnant, close monitoring and tight control of blood glucose levels during the first 9 weeks of pregnancy helps reduce the incidence of birth defects, Schwartz et al. (2000) *Semin Perinatol* 24:120–135.

In approximately 4% of women, pregnancy will induce "gestational diabetes" or "insulin resistance" in women who have never had diabetes before but who have high blood sugar levels during pregnancy. Without enough insulin, the mother become hyperglycemic and is more likely to become hypertensive, Bartha et al. (2000) *Am J Obstet Gynecol* 182:346–350. In addition to the problems this causes the mother, hyperglycemia and hypertension also place the fetus at risk for serious complications. The high maternal levels of glucose are able to cross the placenta, which causes the fetus's pancreas to make extra insulin to metabolize the blood sugar and can lead to macrosomia (alternately called a "fat" baby, or a "big bad baby" (BBB)). Babies with macrosomia face health problems of their own, including damage to their shoulders during birth; breathing problems and hypoglycemia after birth because of their own increased insulin production, Schwartz et al., above. Further, babies with excess insulin become children who are at risk for obesity and adults who are at risk for type 2 diabetes.

Currently, treatment of diabetes during pregnancy is geared toward keeping blood sugar levels below hyperglycemic levels using special meal plans, scheduled physical activity and, if necessary, insulin injections. Monitoring of blood glucose levels after meals is also recommended. Recently, however, it has been suggested that overzealous control of hyperglycemia in pregnancy may lead to hypoglycemic episodes for the mother, Rosenn et al. (2000) *J Matern Fetal Med* 9:29–34. As noted above, maternal hypoglycemia is associated with a variety of problems for the fetus including intrauterine growth retardation, high rates of gestational age-specific neonatal mortality, long term cognitive deficits, increased risk of coronary artery disease, diabetes and hypertension as an adult, Rosenn et al., above. Thus, ideally, blood sugar levels during pregnancy are controlled such that the mother is neither hypoglycemic nor hyperglycemic. Using the methods described herein, which allow for frequent monitoring of blood glucose levels, allows for frequent evaluation of blood glucose levels so that the mother can take appropriate action when either hyperglycemia or hypoglycemia are imminent.

2.2.4 Weight Management

Obesity is a major health problem in many countries and is associated with an increased risk for heart disease, certain cancers and development of Type II diabetes. According to the Centers for Disease Control's (CDC's) National Center for Health Statistics, 54% of adult Americans and between 11% and 14% of children were overweight in 1997, as determined using the Body Mass Index scale, which defines classes of non-obesity and obesity. According to guidelines proposed by the World Health Organization, individuals whose BMI is greater than 25 kg/m$^2$ are Grade 1 overweight. Those whose BMI is greater than 30 kg/m$^2$ are Grade 2 overweight, or obese, and individuals with a BMI greater than 40 kg/m$^2$ are Grade 3 overweight, or morbidly obese (Kopelman (2000) *Nature* 404: 635–643).

According to the CDC, the average American woman is 5'3¾" tall, weighs 152 pounds, and has a BMI slightly greater than 26. A woman of the same height, but whose weight was 231 pounds, would have a BMI of 40 kg/m$^2$. As a person's body mass index increases past 30 kg/m$^2$, the risk of acquiring type 2 diabetes increases sharply. The relative risk of developing type 2 diabetes increases with increasing Body Mass Index (BMI). BMI is measured in kg/m$^2$. Accordingly to Kopelman (Nature 404: 635–643, 2000), obesity is now so common within the world's population that it is beginning to replace under-nutrition and infectious diseases as the most significant contributor to ill health. Obesity is associated with diabetes mellitus, coronary heart disease, certain forms of cancer, and sleep-breathing disorders. Obesity is generally defined by a body-mass index (weight divided by square of the height) of 30 kg m$^{-2}$ or greater. This degree of obesity takes into account neither the morbidity/mortality associated with more modest degrees of a person (or animal) being overweight, nor the detrimental effect of intra-abdominal fat.

Thus, impaired glucose tolerance is a clear risk factor for type 2 diabetes. A survey of American adults performed by the World Health Organization found impaired glucose tolerance in 10%–15% of the study populations. According to the Merck Manual (17$^{th}$ edition), weight loss and exercise are part of the recommended standard treatment for patients with impaired glucose tolerance or type 2 diabetes, and the condition can resolve following weight loss. Furthermore, a recent study correlated weight loss in patients with impaired glucose tolerance and determined that weight loss can also prevent type 2 diabetes from developing in the first place (Eriksson J et al. (1999) *Diabetologia* 42(7): 793–801).

One weight loss program involves eating meals that balance the amounts of protein, fat and carbohydrate. See, e.g., Dr. Barry Sears, *Enter the Zone* (1995), Regan Books. This diet, which is similar to that suggested for diabetic patients, seeks to maintain blood glucose levels within specified ranges by limiting the amount of carbohydrate and fat intake and "balancing" fats and carbohydrates with proteins. Thus, frequent monitoring of blood glucose levels allows subjects following this diet to determine which foods (and what combinations of foods) to eat at what times so they maintain specified blood glucose levels that are neither hyperglycemic nor hypoglycemic.

In sum, using the methods described herein provides an excellent means for (1) demonstrating the need to reduce weight; (2) providing instant evidence of the deleterious effects of obesity; and (3) aiding dieters to monitor blood glucose levels and maintain normal levels by eating appropriately. Isolated finger stick procedures performed during occasional medical exams will most likely not have such an impact. Frequent reminders—be they weekly, monthly, daily or more—of abnormal blood glucose levels, in addition to a thorough education on the potential complications of the condition, will stand a greater chance of inspiring change. The methods described herein can be applied to weight gain, or weight maintenance as well.

Accordingly, in one aspect of the present invention a range of glucose values can be established for a subject based on desired blood glucose levels directed to the desired goal, for example, weight management. Alerts can be set in the glucose monitoring device to be activated when blood sugar levels falls below, or rise above, lower and upper limits (respectively) of the predetermined range. Such alerts provide an on-going assessment of the subject's glucose consumption and production, as well as rates and amounts thereof. Frequent and periodic monitoring of changes in the plasma or blood glucose in a subject provides information to the subject and/or health care profession (e.g., physician, dietician, etc.) that allows optimization of a food plan to suit the particular needs of the subject (for example, weight loss or weight gain).

An appropriate reference range of glucose values (i.e., a low and high threshold value) is typically determined by a trained, health-care professional. Such a reference range may also include a preferred average glucose value, as well as a preferred range of variation around the average value. Such a determination of reference glucose range is typically based on current physical characteristics of the subject (including, but not limited to, body mass index, percentage body fat, hydration level, etc.) and the subject's goal for weight management (i.e., gain, loss, or maintenance). This reference range is then entered into the glucose monitoring device typically with alerts set at the high and low threshold values. One or more microprocessor component of the glucose monitoring device typically includes an algorithm to maintain a record of all subject glucose values determined by the glucose monitoring device. A memory component of the glucose monitoring device may also store related information entered by a subject, such as, times and amounts of exercise, amounts and types of food, etc. Alternatively, such information may be entered into a system that interfaces with the glucose monitoring device, such as, a personal computer (PC), pocket PC, personal digital assistant (PDA, e.g., Palm Pilot™ (Palm Inc., Santa Clara, Calif.)).

Accordingly, a record of glucose levels obtained by frequent sampling (for example, the GlucoWatch biographer provides approximately 3 glucose readings per hour) is developed. Typically, a subject enters the time of meals, snacks, or caloric intake and/or output, in order to keep track of glucose levels relative to such events. Regardless of the subject's inputted information, however, the glucose monitoring device alerts the subject to glucose levels outside of the predetermined range. One set of distinctive alerts may be associated with a low threshold glucose level in order to alert the subject to, for example, consume a snack, and another set of distinctive alerts may be associated with levels above the high threshold value to warn the subject of excessive caloric intake. Further, because an ongoing record of glucose levels is maintained by the glucose monitoring device (and/or an associated device) the records developed over days, weeks, months, etc., can be reviewed by a subject and/or a health-care professional in order to provide appropriate modifications to the food plan. Accordingly, comparing a series of glucose amounts or concentrations as determined by the glucose monitoring device, the record of caloric intake and/or output, and the predetermined reference range of glucose values allows the subject (and/or health-care professional) to evaluate compliance with the reference range of glucose amounts or concentrations that is being used to achieve the weight management goal of the subject. Further, glucose level fluctuations that put the subject at risk can be evaluated and solutions to avoid such fluctuations proposed.

A similar approach may be applied to numerous disease states or conditions, e.g., those described above. For example, a subject may enter information (e.g., time of dosing) about medications that are being taken (such as, HIV medications discussed above) and glucose levels can be evaluated relative to such events, i.e., comparing the record of medication to glucose levels. By keeping track of such information it may be possible to avoid HIV drug-related hyperglycemia and its attendant health problems by modifying the subject's dietary intake, perhaps relative to drug dosing times, in order to maintain glucose values within a predetermined reference range (i.e., between high and low threshold values). Accordingly, by comparing a series of glucose amounts or concentrations in a subject being treated with a pharmaceutical composition (typically comprising at least one non-insulin-containing pharmaceutical compound, further such pharmaceutical compounds typically do not comprise pharmaceuticals used for the treatment of diabetes, rather they are pharmaceutical compounds with associated side-effects on glucose levels) and a reference record of dates/times of treatment with the pharmaceutical, it is possible to evaluate the effect of the pharmaceutical composition on glucose levels in the subject receiving the pharmaceutical composition over time. Further, a reference range of glucose amounts or concentrations that correspond to maintaining a desired range of glucose amounts or concentrations in the subject during a treatment course can be determined by the subject typically in cooperation with a health-care professional. The reference range is typically defined by a high threshold glucose value and a low threshold glucose value. Alerts may be set in the glucose monitoring device to make the subject aware of fluctuations outside of the reference range.

In another aspect, the above-described methods can be applied to a method for improving prognosis and/or reduction of adverse side-effects associated with a disease state or condition in a subject. In this aspect, a reference range of glucose amounts or concentrations is typically determined that corresponds to achieving an improved prognosis or reduction of adverse side-effects associated with said disease state or condition in the subject. The reference range of glucose amounts or concentrations typically comprises a high threshold glucose value and a low threshold glucose value, and further may include a desired average value with a preferred, associated range of variation. The glucose amount or concentration in the subject is monitored using a glucose monitoring device, for example, as described above. A series of glucose values is obtained over a time course. By comparing the series of glucose amounts or concentrations and the reference range compliance with the reference range of glucose amounts or concentrations to achieve an improved prognosis or reduction of adverse side-effects associated with said disease state or condition in the subject can be evaluated. Clearly such monitoring of glucose levels is necessary and useful in diabetic disease, for example, type I and type II diabetes, however, the method is useful when applied to monitoring glucose in disease states or conditions where the primary effect of the disease state or condition is not directly on glucose levels in the subject, numerous such disease states and conditions are outlined above, including, but not limited to cancer remission, infection with human immunodeficiency virus (HIV), infection with *Candida*, long distance driving, organ transplantation, growth hormone therapy, renal failure, infection with malaria, alcoholism, intense exercise, cardiovascular disease, cystic fibrosis, stroke, and ischemia.

As another example, the above-described method of providing a functional range of glucose values can be extended to endurance exercise and training. Different ranges of glucose can be established by the subject and/or a health-care professional wherein a selected range of glucose values is put into effect in the glucose monitoring device depending on the activity. For example, three reference glucose ranges may be established for a person undertaking an exercise or training program: a resting range of glucose values, where the high and low glucose threshold values are determined to maintain a certain weight, an aerobic-exercise range of glucose values, where the high and low glucose threshold values are determined to maintain optimum performance during aerobic exertion, and a training-exercise range, where most of the activity is not aerobic in nature (e.g., weight training) and the high and low glucose threshold values are determined to maintain optimum performance during the training activity. A subject may activate a selected set of range values in the glucose monitoring device. A default setting may be selected by the subject to which settings the glucose monitoring device returns after a specified amount of time, or another alert may be programmed to remind the subject to change the selected set of range values after a certain period of time. In this embodiment of the present invention, a record of glucose level variation correlated to activities gives the subject information to evaluate which may reveal particular issues that need to be addressed. For example, consistently low glucose levels during sustained aerobic events may indicate to the subject that such events should be preceded by an increased intake in carbohydrates/fats/proteins. Further, review and evaluation of such a record (obtained over, for example, days, weeks, or months) may allow the subject to modify the intensity, duration, and/or type of exercise in order to maintain appropriate glucose levels throughout the subject's training program, thereby preventing over-exertion and/or reduction of muscle mass.

In an alternative embodiment, high and low glucose threshold values may be established for a reference glucose range. The glucose monitoring device may be worn by the subject in order to obtain frequent, periodic measurements of glucose amount or concentration in the subject. An independent record may be kept by the subject of caloric intake (e.g., meals and snacks) as well as caloric expenditure (e.g., exercise). This independent record can then be compared to the record of glucose values provided by the glucose monitoring device and the reference range of glucose values. Such comparison may be carried out by hand or by a computerized algorithm. In this aspect of the invention, trends of glucose levels can be compared to caloric intake/output and diet and exercise adjusted accordingly to achieve weight management goals. Accordingly, comparing a series of glucose amounts or concentrations as determined by the glucose monitoring device, the record of caloric intake/output, and the predetermined reference range of glucose values allows the subject (and/or health-care professional) to evaluate compliance with the reference range of glucose amounts or concentrations that is being used to achieve the weight management goal of the subject. Such independent record keeping by the subject may be applied to other disease states or conditions described above (e.g., medications, exercise training, long distance driving, etc.).

Although preferred embodiments of the subject invention have been described in some detail, it is understood that obvious variations can be made without departing from the spirit and the scope of the invention as defined by the appended claims.

What is claimed is:

1. A method for monitoring an effect of at least one non-insulin-containing pharmaceutical composition on glucose levels in a subject receiving said pharmaceutical composition, the method comprising:

monitoring glucose amount or concentration in the subject by a glucose monitoring method comprising:

transdermally extracting a sample comprising glucose from the subject using a sampling system that is in operative contact with a skin or mucosal surface of said subject, wherein the extracting is carried out using an iontophoretic system comprising first and second iontophoretic electrodes;

contacting the sample with a sensor element in the presence of glucose oxidase that reacts with glucose to produce hydrogen peroxide;

detecting the hydrogen peroxide with the sensor element that reacts electrochemically with the hydrogen peroxide to produce a detectable signal, wherein said detectable signal is specifically related to glucose amount or concentration in the subject;

measuring the detectable signal;

correlating the signal measurement to an amount or concentration of glucose in the subject; and repeating said glucose monitoring method to obtain a series of glucose amounts or concentrations, in the subject, at selected time intervals;

maintaining a record of treatment with the pharmaceutical composition; and comparing said series of glucose amounts or concentrations and said record to evaluate the effect of the pharmaceutical composition on glucose levels in the subject receiving said pharmaceutical composition, wherein the pharmaceutical composition is not used in the subject for the treatment of diabetes and is selected from the group consisting of pentamidine, quinine, saquinavir and indomethacin.

2. The method of claim 1 further comprising, determining a reference range of glucose amounts or concentrations that correspond to maintaining a desired range of glucose amounts or concentrations in the subject during a treatment course with said pharmaceutical composition, wherein said reference range comprises a high threshold glucose value and a low threshold glucose value.

3. The method of claim 2, wherein said monitoring glucose amount or concentration in the subject by a glucose monitoring method further comprises providing an alert to the subject when a glucose amount or concentration, in the subject, at a selected time interval falls outside of the reference range.

4. The method of claim 1, wherein the subject is also receiving insulin.

* * * * *